(12) United States Patent
Shusterman et al.

(10) Patent No.: US 6,814,076 B2
(45) Date of Patent: Nov. 9, 2004

(54) AMBIENT PRESSURE CONTROL VENTILATION APPARATUS AND METHOD

(76) Inventors: Taly Shusterman, 17/4 Hameyasdim Street, Nahariya (IL), 22402; Mark Shusterman, 17/4 Hameyasdim Street, Nahariya (IL), 22402

( * ) Notice: Subject to any disclaimer, the term of this patent is extended or adjusted under 35 U.S.C. 154(b) by 0 days.

(21) Appl. No.: 10/220,178
(22) PCT Filed: Jan. 29, 2001
(86) PCT No.: PCT/IL01/00085
  § 371 (c)(1),
  (2), (4) Date: Aug. 27, 2002
(87) PCT Pub. No.: WO01/62324
  PCT Pub. Date: Aug. 30, 2001

(65) Prior Publication Data
  US 2003/0205230 A1 Nov. 6, 2003

(30) Foreign Application Priority Data
  Feb. 27, 2000 (IL) .............................................. 134742

(51) Int. Cl.[7] .............................................. A62B 31/00
(52) U.S. Cl. ........................... 128/205.26; 128/204.18; 128/204.23; 128/204.21
(58) Field of Search ..................... 128/202.12, 205.26, 128/204.18, 204.23, 204.21, 205.13, 205.17; 600/21, 22

(56) References Cited

U.S. PATENT DOCUMENTS

| | | | | |
|---|---|---|---|---|
| 4,467,798 A | * | 8/1984 | Saxon et al. ............ | 128/205.26 |
| 4,770,165 A | * | 9/1988 | Hayek ......................... | 601/43 |
| 5,255,673 A | * | 10/1993 | Cardwell et al. ....... | 128/202.12 |
| 5,360,001 A | * | 11/1994 | Brill et al. .............. | 128/205.26 |
| 5,503,143 A | * | 4/1996 | Marion et al. ......... | 128/202.12 |
| 5,871,008 A | * | 2/1999 | Poon et al. ............. | 128/202.12 |
| 5,988,166 A | * | 11/1999 | Hayek ................... | 128/205.26 |
| 6,016,803 A | * | 1/2000 | Volberg et al. ......... | 128/205.26 |
| 6,352,076 B1 | * | 3/2002 | French ................... | 128/203.12 |

* cited by examiner

Primary Examiner—Henry Bennett
Assistant Examiner—Mital Patel
(74) Attorney, Agent, or Firm—Reed Smith LLP; William H. Dippert

(57) ABSTRACT

An ambient pressure control ventilation apparatus controls mechanical ventilation of a patient. The apparatus comprises: a sealable chamber adapted to accommodate a while body of a patient, a pump fluidically connected to the chamber, alternatively compressing and decompressing a ventilating gas within the chamber: a relief valve, fluidically connected to the chamber: and a control unit adapted to control the pump and the relief valve so as to create a periodic regime of alternating compression and decompression of ventilating gas within the chamber, about a predetermined baseline.

9 Claims, 2 Drawing Sheets

AMBIENT PRESSURE CONTROL VENTILATION APPARATUS AND METHOD

FIELD OF THE INVENTION

The present invention relates to mechanical ventilation systems. More particularly, it relates to mechanical respiratory assistance by ambient pressure control ventilation in a close chamber.

BACKGROUND OF THE INVENTION

Assisted or artificial respiratory actions on patients are often used in medical practice. Two types of ventilation methods are generally used: positive pressure ventilation, when periodic positive airway pressure is applied on patients airways and lungs, and negative pressure ventilation (iron lungs) when the patient's chest region is enclosed by an enclosure in which subatmospheric pressure is applied periodically.

Those main traditional methods of mechanical respiratory assistance such as positive airway pressure ventilation as well as "iron-lungs" are known to have a lot of physiological adverse effects, technical disadvantages and pitfalls. The main disadvantages of positive pressure methods of ventilation stem from the need to inflate the gas mixture into the patient's airway and lungs with such a positive pressure that its range is comparable with right and left heart ventricles filling pressures. This can interfere with the venous blood return to the heart that may result in hemodynamic deterioration, especially in patients that suffer from hypovolemia, compromised cardiac function, lung and chest problems and shock. Furthermore, patient's suffering from these diseases are already in poor medical condition, and their body is very likely not to withstand the strenuous procedure. Positive pressure ventilation may also result in barotrauma of airway and lungs with possible development of life threatening complications. Long time exposure to positive pressure ventilation may result also in the development of lung atelectasis and/or secondary infection, which is directly related to the duration of the mechanical positive pressure ventilation. Positive pressure ventilation also requires the inflation of endotracheal tube balloon with such pressures that on one hand, it establishes airway sealing, but on the other hand it may result in severe damage to the tracheal mucosa and tracheal wall, potentially leading to very dangerous complications, such as tracheal wall and great mediastinal vessels rupture.

Negative pressure ventilation, as opposed to positive pressure ventilation, is free from problems related to venous return and cardiovascular deterioration as well as barotrauma development. There are problems that arise from the employment of negative pressure ventilation. The need to accommodate the patient's body in an enclosure requires the use of sealing means that are very difficult to fit on the patient's neck, chest and abdomen. It is especially difficult in pediatric population or in uncooperative patients as well as during prolonged mechanical ventilation. Negative pressure ventilators are very difficult to use in weaning from mechanical ventilation.

Improvements of mechanical respiratory systems are known in the art. An example of such system that encloses the chest region is disclosed in U.S. Pat. No. 4,815,452 "VENTILATOR APPARATUS AND FLUID CONTROL VALVE", filed in 1988 by Z. Hayek. One aspect of the invention provides a patient enclosure for ventilator apparatus comprising a base member and a liftable cover member which in an operative position defines a patient receiving chamber having at least one aperture in the cover member for accommodating a portion of the patient's body, the or each such aperture in the cover member being open along an edge of the cover member which overlies the base member in the operative position and containing a seal member for forming a substantially airtight seal in use between the cover member and the patient's body and the base member, wherein the seal member takes the form of a flexible curtain having a free edge overlying the base member and means for tensioning a portion of the curtain to cause the curtain to seal against the base member and the patient's body.

Another enclosure for ventilation is disclosed in EP patent No. 0379049 "CHEST ENCLOSURE FOR VENTILATORS" published in 1990 by Z. Hayek. This chest enclosure is used for introducing assisted ventilation for the lungs of a patient, when combined with an air oscillator. The chest enclosure comprises a stiff but flexible plastic tunnel member adapted to cover the chest, provided at its upper and its lower end with an air-impermeable flexible cushion, a band of flexible material extending from along the entire lateral edges of the tunnel, said bands extending to behind the back of the patient in an overlapping relationship, means being provided for the attachment of the bands with each other, an air passageway being provided into the enclosure for connection to an air oscillator.

Ventilators of this type provide an apparatus in which at least the patient's head protrudes from the enclosure. In order to enable pressure changes in the enclosure, sealing the enclosure from the surrounding is necessary. Sealing the enclosure promotes problems and can also delay the commencing of assisted respiration, which potentially may cause damage to the patient.

The use of a pressurized container in which the whole body is enclosed was developed for blood oxygenation in premature neonates. The method is disclosed in U.S. Pat. No. 5,582,574 "HYPERBARIC INCUBATION METHOD" filed in 1995 by F. S. Cramer. This pressurized container is filled with pure oxygen. The apparatus, and the method of treatment provided thereby, are able to deliver oxygen to the blood of an enclosed premature neonate by means of directly diffusing molecular oxygen through the unusually permeable skin of such infants. Hyperbaric pressure, i.e., pressure substantially above one atmosphere absolute (ATA), preferably at least two ATA, is maintained in the container, which facilitates the transcutaneous delivery of oxygen to the blood. Means are included for protecting the eyes of the neonate and for performing physiological ventilation of the lungs thereof. The provision of normal tissue oxygen tensions facilitates the neurological development of the infant, thereby enhancing its long-term quality of life.

BRIEF DESCRIPTION OF THE INVENTION

It is a purpose of the present invention to provide new ambient pressure control ventilation apparatus for mechanical ventilation of a patient. The patient is placed inside a sealed chamber wherein within that chamber periodic changes of pressure are applied.

It is another purpose of the present invention to provide an ambient pressure control ventilation apparatus for mechanical ventilation applicable in cases were traditional mechanical ventilation fails. These cases include among others patients with hemodynamic deterioration such as hypovolemia, compromised cardiac function, marginal cases of respiratory distress syndrome, chest, airway and lung trauma and bleeding, and asthmatic attack.

Yet another purpose of the present invention is to provide an ambient pressure control ventilation apparatus for home ventilation which is safer for users and provide more comfort conditions for patients suffering from chronic respiratory failure who need negative or positive pressure ventilators for home use, especially in pediatric and uncooperative populations.

Still another purpose of the present invention is to provide an ambient pressure control ventilation apparatus for weaning from mechanical ventilation.

It is another purpose of the present invention to provide an ambient pressure control ventilation apparatus for patients with chest, neck and abdomen deformity, scars, chronic infections, burns etc., which make positive pressure ventilation difficult and negative pressure ventilation impossible.

Yet another purpose of the present invention is to provide an ambient pressure control ventilation apparatus for the treatment of patients suffering from congestive heart failure. The outpatient, home or intermittent overnight use of the novel apparatus enables decreasing at least part of the patient's medication intake.

It is another purpose of the present invention to provide an ambient pressure control ventilation apparatus for patients having prophylactics of deep and superficial venous thrombosis that enables elimination of anticoagulation treatment.

It is another purpose of the present invention to provide an ambient pressure control ventilation apparatus for substitution of intraortic balloon counterpulsation (IABC) device.

Another purpose of the present invention aims at providing an ambient pressure control ventilation apparatus for substitution of advanced closed cardiac massage devices (Cardiopump, Four-phase Life-stick etc.).

It is thus provided an ambient pressure control ventilation apparatus for mechanical ventilation of a patient comprising:
- a sealable chamber adapted to accommodate a whole body of a patient,
- a pump fluidically connected to said chamber adapted to alternatively compress and decompress a ventilating gas within said chamber;
- a relief valve, fluidically connected to said chamber; and
- a control unit adapted to control said pump and said relief valve so as to facilitate a periodic regime of alternating compression and decompression of said ventilating gas within said chamber, about a predetermined baseline.

Furthermore, in accordance to another preferred embodiment of the present invention, said ventilating gas is a mixture of air and oxygen.

Furthermore, in accordance to another preferred embodiment of the present invention, said ventilating gas is oxygen.

Furthermore, in accordance to another preferred embodiment of the present invention, said apparatus further comprising at least one pressure sensor within said chamber, said at least one pressure sensor communicating with said control unit so as to allow said control unit to determine the pressure condition within said chamber.

Furthermore, in accordance to another preferred embodiment of the present invention, said control unit is further adapted to prevent oxygen partial pressure drop within said chamber below a predetermined pressure value.

Furthermore, in accordance to another preferred embodiment of the present invention, said predetermined pressure value is 0.25 atm.

Furthermore, in accordance to another preferred embodiment of the present invention, said baseline ranges between 0.5 atm. and 1.5 atm.

Furthermore, in accordance to another preferred embodiment of the present invention, said control unit is adapted to control said pump and said relief valve so as to facilitate a periodic regime of alternating compression and decompression of said ventilating gas within said chamber, about a predetermined baseline, within a predetermined pressure range of the baseline plus 170 mm Hg to the baseline minus 170 mm Hg.

Furthermore, in accordance to another preferred embodiment of the present invention, said control unit is adapted to control said pump and said relief valve so as to facilitate a periodic regime of alternating compression and decompression of said ventilating gas within said chamber, about a predetermined baseline, within a predetermined pressure range of between the ambient barometric pressure to the ambient barometric pressure plus 175 mm Hg.

Furthermore, in accordance to another preferred embodiment of the present invention, said chamber is transportable.

Furthermore, in accordance to another preferred embodiment of the present invention, said chamber is provided with wheels for transportation.

Furthermore, in accordance to another preferred embodiment of the present invention, said chamber is essentially made of non-compliant transparent plastic material.

Furthermore, in accordance to another preferred embodiment of the present invention, said chamber is provided with a door adapted to allow quick bringing in and taking out of a patient.

Furthermore, in accordance to another preferred embodiment of the present invention, said door can also be opened and closed from within said chamber.

Furthermore, in accordance to another preferred embodiment of the present invention, said chamber is provided with a sealable opening adapted to allow quick access of a nursing team to the airway and chest area of said patient.

Furthermore, in accordance to another preferred embodiment of the present invention, a bed is provided in said chamber for the patient to lie on.

Furthermore, in accordance to another preferred embodiment of the is present invention, The apparatus as claimed in claim 1, wherein said chamber is provided with a communication block that is adapted to facilitate linking of devices positioned within said chamber to said control unit or other devices.

Furthermore, in accordance to another preferred embodiment of the present invention, monitoring lines from sensors placed in an endotracheal tube within the airway of the patient are connected via said communication block to said control unit.

Furthermore, in accordance to another preferred embodiment of the present invention, a reserve oxygen balloon is provided for emergency cases.

Furthermore, in accordance to another preferred embodiment of the present invention, said chamber is further provided with a highly compliant breathing bag that is designed to be connected to the airway of the patient.

Furthermore, in accordance to another preferred embodiment of the present invention, said pump is electrically connected to the main electric supply.

Furthermore, in accordance to another preferred embodiment of the present invention, a reserve battery adapted to supply electricity to said pump is provided for cases of emergency.

Furthermore, in accordance to another preferred embodiment of the present invention, there is provided an ambient pressure control ventilation method for mechanical ventilation of a patient comprising the following steps:

1. providing a sealable chamber adapted to accommodate a whole body of a patient;
2. providing a pump fluidically connected to said chamber adapted to alternatively compress and decompress a ventilating gas within said chamber;
3. providing a relief valve, fluidically connected to said chamber;
4. providing a control unit adapted to control said pump and said relief valve so as to facilitate a periodic regime of alternating compression and decompression of said ventilating gas within said chamber, about a predetermined baseline;
5. placing a whole body of a patient in said sealable chamber; and
6. providing a periodic regime of alternating compression and decompression of a ventilating gas within said chamber, about a predetermined baseline.

Furthermore, in accordance to another preferred embodiment of the present invention, said ventilating gas is a mixture of oxygen and air.

Furthermore, in accordance to another preferred embodiment of the present invention, said baseline ranges between 0.5 atm. and 1.5 atm.

Furthermore, in accordance to another preferred embodiment of the present invention, the periodic regime of alternating compression and decompression of said ventilating gas within said chamber alternates between said baseline plus 170 mm Hg to said baseline minus 170 mm Hg.

Furthermore, in accordance to another preferred embodiment of the present invention, the baseline is the ambient barometric pressure.

Furthermore, in accordance to another preferred embodiment of the present invention, the periodic regime of alternating compression and decompression of said ventilating gas within said chamber, alternates between the ambient barometric pressure to the ambient barometric pressure plus 175 mm Hg.

Furthermore, in accordance to another preferred embodiment of the present invention, the periodic regime of alternating compression and decompression of said ventilating gas within said chamber, alternates between the ambient barometric pressure minus 90 mm Hg to the ambient barometric pressure plus 90 mm Hg.

Furthermore, in accordance to another preferred embodiment of the present invention, said method further comprises the step of compressing into said chamber an additional volume of oxygen upon an oxygen partial pressure drop below a predetermined value within said chamber.

Finally, in accordance to another preferred embodiment of the present invention, said predetermined value is 0.25 atm.

BRIEF DESCRIPTION OF THE FIGURES

In order to better understand the present invention, and appreciate its practical applications, the following Figures are provided and referenced hereafter. It should be noted that the Figures are given as examples only and in no way limit the scope of the invention as defined in the appending claims. Like components are denoted by like reference numerals.

DETAILED DESCRIPTION OF THE INVENTION AND FIGURES

Boyle's law states that the volume of a certain amount of gas is inversely proportional to the pressure, the temperature remaining constant. The physiological application of Boyle-Marriott's law describes the gas volume in the lungs of a patient placed in a closed chamber, wherein periodic changes of barometric pressure are applied. It is known that when the barometric pressure varies in the range between 0.75 to 1.25 atmospheres in a sealed chamber, the temperature does not change significantly, i.e., there is no change in temperature when using a thermometer of 0.1° C. accuracy.

Figure 1:
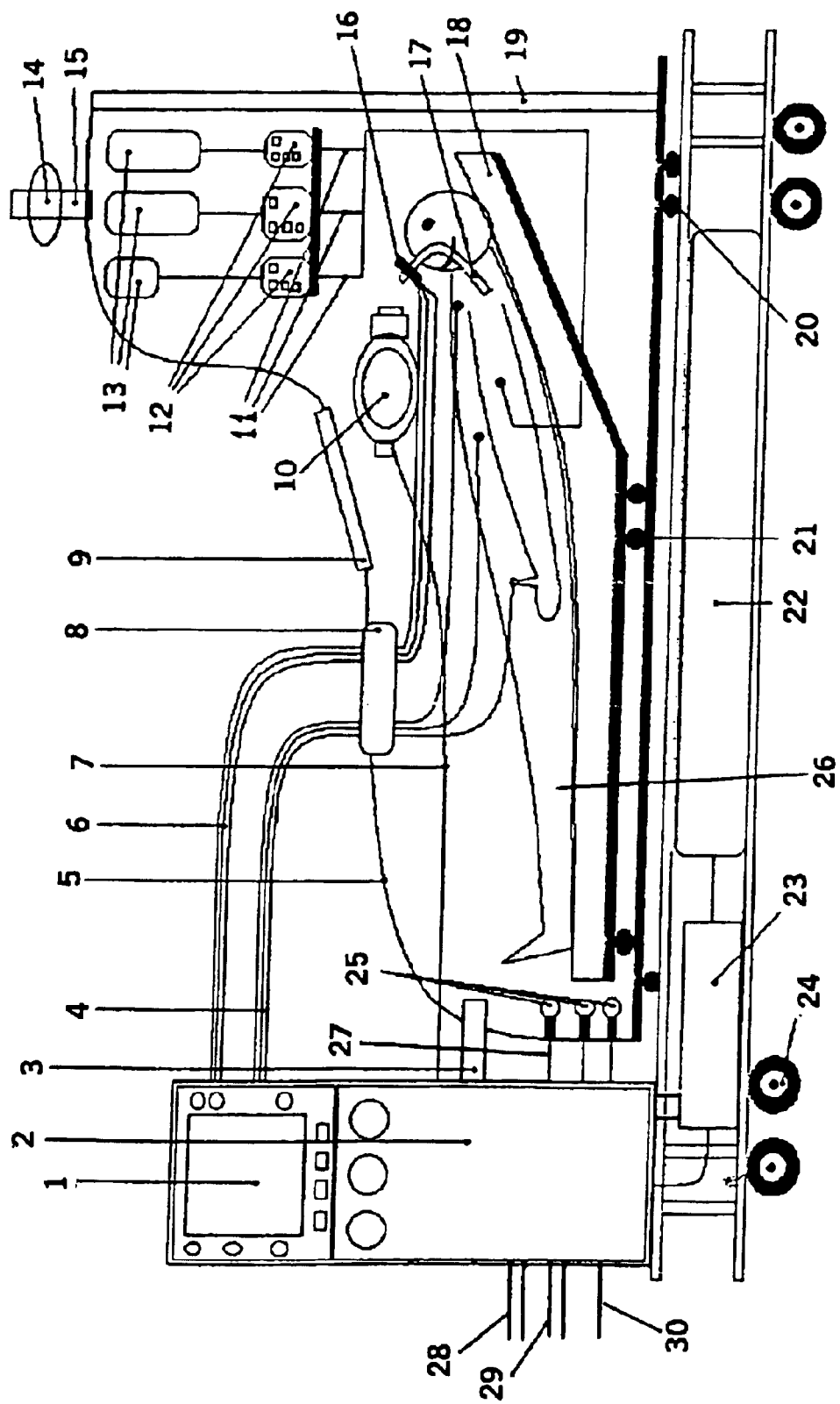
FIG. 1 illustrates an ambient pressure control ventilation apparatus for mechanical respiratory assistance in accordance to a preferred embodiment of the present invention.

A preferred embodiment for an ambient pressure control ventilation apparatus of the present invention is based on the physiological application of Boyle-Marriott's law. Reference is now made to FIG. 1, which illustrates an ambient pressure control ventilation apparatus for mechanical respiratory assistance. The ambient pressure control ventilation apparatus comprises a non-compliant chamber 5 that is preferably made of a transparent plastic material (maybe with metal enforcement etc.) and may be designed in any preferable shape according to the needs of the patients and the local conditions, provided the patient's entire body is enclosed within that chamber. Chamber 5 is equipped with at least two doors capable of sealingly block gas from leaking in or out of the chamber. The first door 19 is adapted to enable a quick bringing in and taking out of the patient and the other door 9 is adapted to allow quick access of the nursing team to the patient's airway and chest area in case of emergency. In an ambient pressure control ventilation apparatus designed for cooperative and conscious patients, it is recommended to provide the patient with the facility to open and close door 19 and control totally or partially the physiological parameters of the apparatus from within chamber 5. The volume of chamber 5 is adapted to be minimal but in the same time is designed to be comfortable for the patient according to his needs (i.e. if the patient requires laying down or can be seated, etc.).

Chamber 5 is mounted on a carrying vehicle 24 such as a trolley and can be easily disengaged from the trolley. Carrying vehicle 24 permits easy intrahospital transportation of the chamber with the patient in it for usual needs such as transfer from a ward to an ambulance, from room to room etc. Inside chamber 5, a mattress 18 such as the one used on intensive care unit beds is provided. Mattress 18 can be taken out of chamber 5 and placed again inside the chamber using wheels 21.

A theoretical account is hereby provided, with respect to the volumes and pressures in the lungs of a paralyzed patient having an open airway that is placed in a closed chamber with periodic changes in the barometric pressure inside that chamber. At normal barometric pressure, the lungs are filled with gas having the same pressure as the ambient pressure within the chamber. The transpulmonary pressure is zero. The lung's volume is determined only by the intrinsic properties of the lungs and chest. After an increase in the barometric pressure in the chamber while the airways remain open, the airway pressure and the ambient pressure equalize following a certain period of time called airway time constant, so that the transpulmonary pressure becomes zero again and the lungs volume is the same as before. It is important to notice that the mass of gas in the same volume increases proportionally to the barometric pressure change, provided the temperature is constant.

It is known that normal tidal volume in children and adults is about 7 ml/Kg including 2–3 ml/kg of dead space. Normal functional residual capacity (FRC) ranges from 27–30 ml/Kg in newborns to 30 ml/Kg in adults, so that $V_{inSp}$ divided by $V_{exp}$ equals about 1.23. Thus, according to Boyle's law and Klapeyron's formula, a pressure difference of about 0.23 atmospheres is required in order to introduce such mass of gas to the lungs that is sufficient to sustain normal breathing parameters. A pulmonary gas exchange is originated while transpulmonary pressure and the range of airway, lungs and chest movements in the method of the present invention is less than the transpulmonary pressure and the range of airway, lungs and chest movements in any prior art traditional method of ventilation. This aspect was tested and proved on computerized model, an experimental model and animal pilot study.

An intake tube 3 and an exhaust tube 15 equipped with pressure relief valve 14 are provided, fluidically connected to chamber 5. Relief valve 14 is fluidically connected to a compression or decompression pump 2, or a pump capable of performing both tasks. The intake and exhaust tubes ventilate chamber 5 in a minimal flow rate that suffice the provision of $O_2$ and $CO_2$ gradient formation according to the patient's needs. Relief valve 14 may be digitally controlled in order to create the necessary pressure changes in chamber 5. When relief valve 14 is closed, and fresh gas flows through intake tube 3 into chamber 5 (pumped in by pump 2), the pressure in the chamber rises, and when valve 14 is open, the pressure in the chamber decreases. If subatmospheric pressure is needed for patient ventilation, the system is capable of performing withdrawal of gas from chamber 5, by activating the pump to create subatmospheric pressure levels within chamber 5, and upon opening valve 14 air is allowed to enter the chamber through exhaust tube 15. The apparatus is designed in such a way that permits the formation of a subatmospheric baseline pressure and positive and negative periodic changes of the pressure around this baseline. The baseline pressure and the pressure changes are adapted to the clinical conditions as will be explained further on.

It is important to notice that in any case in which subatmospheric pressure levels are required according to the clinical conditions of the patient, a control unit 1 does not allow a drop in the partial pressure of oxygen inside chamber 5 so that it is kept higher than 0.25 atm. To compensate on the decrease in the barometric pressure in the chamber, pump 2 insufflate additional volume of oxygen until the desired oxygen partial pressure is achieved (in any case more that 0.25 atm., in accordance with the current standards of anesthesia machines).

Figure 2:
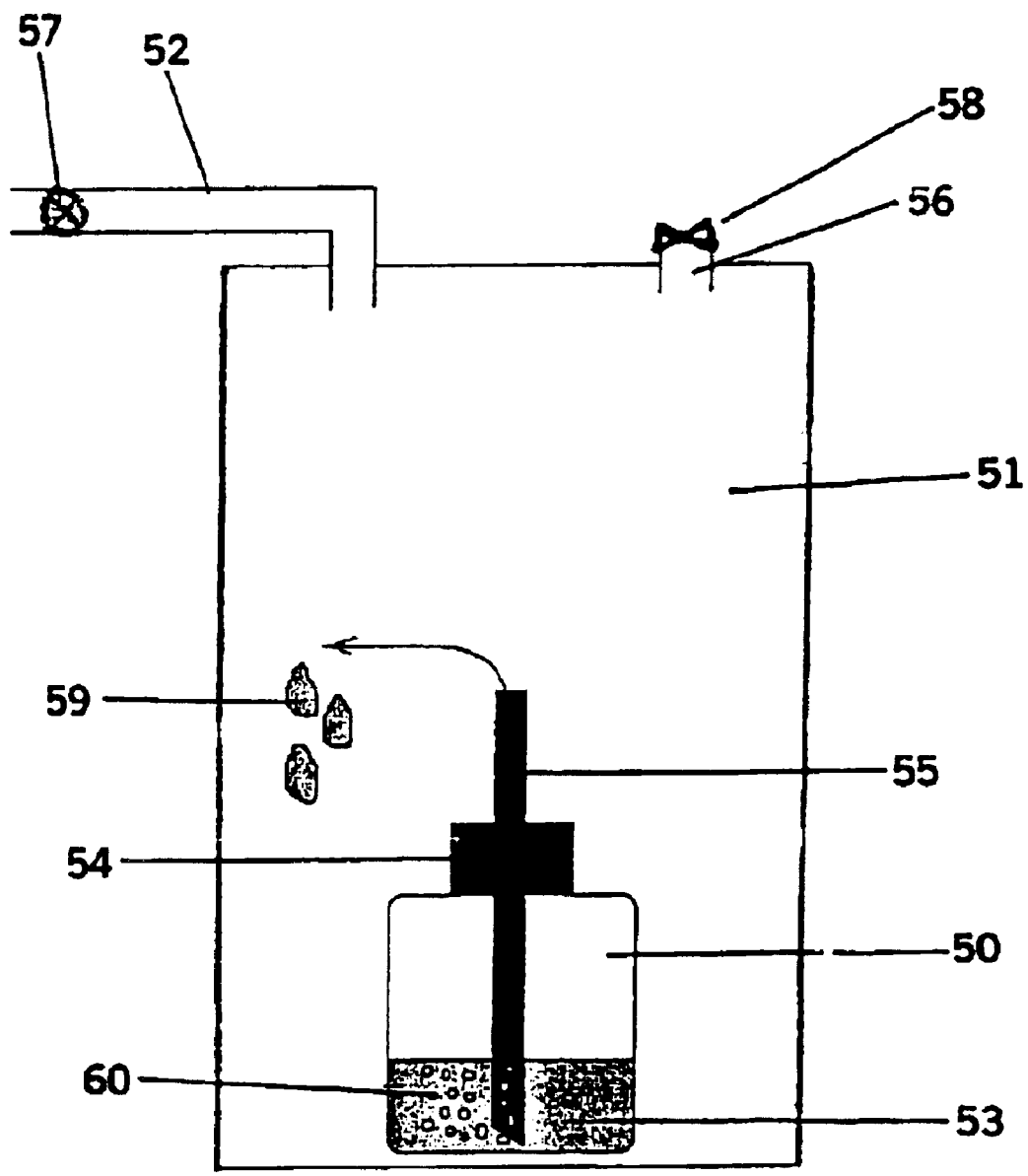
FIG. 2 illustrates a simplified experimental model apparatus that imitates lungs of a patient in a vacuum chamber, built according to the principles of the present invention.

The principle validity of the ambient pressure control ventilation apparatus is illustrated using a simplified model shown in FIG. 2. Reference is now made to FIG. 2 illustrating a simplified experimental model apparatus that imitates lungs of a patient in a vacuum chamber, built according to the principles of the present invention, with a bottle replacing the lungs of a potential patient.

A compliant transparent plastic bottle 50 was placed in a transparent, noncompliance plastic chamber 51 that is connected to a vacuum pump (not shown in the Figure) through tube 52. A vacuum port 57 was connected to tube 52. Plastic bottle 50 was designed to imitate the lungs of a patient. Plastic bottle 50 was partially filled with water 53 and tightly closed by hermetic cover 54 through which a standard endotracheal tube of compatible size 55 was inserted. Chamber 51 was also provided with an exhaust tube 56 having a valve 58 that can be periodically opened or closed. During suctioning of chamber 51 and periodic opening of valve 58, the desired barometric pressure changes in the internal space of chamber 51 were established. During the experiment, the following observations were made:

1. During barometric pressure decrease, water 59 ejected from bottle 50 through endotracheal tube 55 to chamber 51.
2. During barometric pressure increase, gas bubbles 60 were observed in water 53: air entered from chamber 51 to bottle 50 through endotracheal tube 55.
3. There were no visible movements of the outer walls of bottle 50 during the barometric pressure changes, although the bottle was made of compliant plastic.
4. The variations in pressure were conducted periodically, in about 60 cycles per minute, and accordingly surges of water 59 from bottle 50 and bubbling of gas bubbles 60 in water 53 were observed with similar rate.
5. The experiment was performed using three different bottles with marginally different compliance from extremely low (glass bottle) to extremely high (very thin wall plastic bottle). Standard lung imitator for check up of anesthesia and intensive care machines was also used in this experiment. It is important to notice that in all four experiments the same results were obtained in spite of different compliance of the bottles and lung imitator.

Returning to FIG. 1, chamber 5 is provided with a communication block 8 that is designed to enable safe passage of monitoring lines 4 from the patient's body and lines 6 from sensors 16 in an endotracheal tube 17 to control unit 1, or other devices. Physiological and respiratory parameters of the patient's ventilation according to current standards of intensive care unit and anesthesia machines are collected using endotracheal tube sensors 16 from an endotracheal tube 17 and from a patient's body 26.

Infusion bags 13 and infusion devices 12 are placed inside chamber 5, each bag is connected through an infusion line 11 to patient 26 lying on mattress 18.

The pressure in chamber 5 is measured by a pressure sensor, in this embodiment, a pressure gauge 25 that is communicating with control unit 1. Monitoring lines 4 and endotracheal tube sensors lines 6 from within the chamber are linked through communication block 8 to control unit 1, on which the collected parameters may be displayed. Control unit 1 also collects data from pressure gauge 25 via lines 27 so that feedback control of the pressure can be performed, too. Control unit 1 is electrically connected to pump 2 and to relief valve 14 and controls the actuation of the pump and the valve (independently) in a predetermined manner, which is explained hereafter.

Pump 2 is provided with pipelines supplying air 28 and oxygen 29. In regular operation conditions, a mixture of air and oxygen is ventilated into the chamber. There are situations in which a compansating amount of oxygn is needed. For example, to compensate on a possible decrease in the barometric pressure in chamber 5, pump 2 insufflate additional volume of oxygen as explained before.

Pump 2 is electrically connected to an electric supplier 30. For cases of electricity failure emergencies, a reserve battery 23 is provided in the vicinity of the chamber. Reserve battery 23 may be mounted on carying vehicle 24. In addition, a reserve oxygen tank 22 is mounted on carying vehicle 24 for emergency cases.

Highly compliant breathing bag such as Ambu bag 10 is designed to be connected via standard connectors to the patient's airway 17. Ambu bag 10 is designated for emergency patient's assisted ventilation in cases of technical failure of the system. The nursing team is capable to assist in the ventilation of the patient through door 9. The second purpose of Ambu bag 10 is to provide a possibility in which the ambient pressure control ventilation of the patient's lungs will be performed through the Ambu bag while using much less pressure difference of the relatively high compliance of the Ambu bag in comparisson with the patient's chest and lung compliance. Additional oxygen line 7 connects pump 2 and Ambu bag 10.

The ambient pressure control ventilation apparatus has many advantages over the traditional ventilation systems. The application of an excessive pressure on the whole body instead of only on the torso results in squeezing of the capacitance vessels, increasing venous return, right ventricle filling and output that results in increased pulmonary perfusion during the phase of maximal pulmonary gas filling (maximal partial pressure of oxygen). This fact may improve the ventilation/perfusion ratio. At the same time, the barometric pressure (BP) elevation during the operation of the ambient pressure control ventilation apparatus increases $PaO_2$ according to $PaO_2=(BP-47)*FiO_2—PaCO_2/RQ$.

The ambient pressure control ventilation apparatus, when operated in regular conditions, can have impact on systemic vascular resistance and on the heart rate that may result in beneficial or, in extreme cases, detrimental effect. In cases of hemodynamic deterioration (for example: patients with aortic or mitral regurgitation) it is possible to manipulate the barometric pressure gradient to be regulated from normal BP−90 mm Hg to normal BP+90 mm Hg, for example, instead of normal BP to normal BP+175 mm Hg in regular conditions. This also manipulates the functional residual capacity and the upper and lower airway diameter and dynamic resistance that may be decreased according to the decrease of the ambient pressure. It is probable that in contrast to normal breathing and traditional mechanical ventilation, the airways may paradoxically expand during expiration, loosing part of the resistance and/or the ability to intrinsic positive and expiratory pressure (PEEP) formation.

Another advantage of the use of the ambient pressure control ventilation apparatus is the minimal, if at all, increase of transpulmonary and intrathoracic pressures. Accordingly, there is a minimal, if at all, interference with blood drainage from the brain, a possible implication during treatment of high intracranial pressure.

It was mentioned that much less transpulmonary pressure is needed during ambient pressure control ventilation in the apparatus of the present invention. Therefore, this apparatus can have a vital role in the treatment of bronchopleural fistulas, airway trauma or in postoperative ventilation after airway surgery.

Traditional positive pressure ventilation is more difficult when native lung and/or chest compliance decreases. In contrast with positive pressure ventilation, the ambient pressure control ventilation may be even more effective when native lung and/or chest compliance decrease. Therefore, other possible applications of the apparatus may include adult respiratory distress syndrome, pneumonia, bronchial asthma (attack) or uncontrolled intrinsic PEEP elevation (OR, ICU).

According to the ability of ambient pressure control ventilation to squeeze superficial veins and to increase preload to the right ventricle of the heart without medication and fluid loading, the apparatus may be beneficial for patients suffering from congestive heart failure.

In the same principle of superficial vascular squeezing, ambient pressure control ventilation may substitute deep venous thrombosis prophylaxis, so the need of anticoagulant treatment may be partially or fully eliminated. As mentioned above, ambient pressure control ventilation most probably has an impact on systemic vascular resistance. Being applied to the whole body with rate of patient's pulse, such pressurizing like ambient pressure control ventilation synchronized with electrocardiogram tracing may substitute intraortic balloon counterpulsation (IABC). In the last case, inflation phase of ambient pressure control ventilation must be synchronized with heart diastola, effectively simulating physiologic events of IABC.

The ability of ambient pressure control ventilation to interfere with venous blood flow through superficial veins and its influence on systemic vascular resistance may open the way to nonpharmacological intervention in right and left congestive heart failures, and nonpharmacological DVT prophylaxis.

According to the basic principles of modern cardiopulmonary resuscitation (CPR), whole-body squeezing obtained in ambient pressure control ventilation may serve as more effective priming technique than traditional and advanced methods of close cardiac massage (Cardiopump and Four-phase Life-stick). In order to use the ambient pressure control ventilation apparatus for this purpose, closure of the endotracheal tube is synchronized with the pressure elevation in the chamber in such a manner that permits optimal cardiac priming. The pressure elevation is applied with the rate that enables optimal combination of cardiac priming/output and pulmonary gas exchange.

Moreover, application of ambient pressure control apparatus synchronized with spontaneous heart activity via EKG or arterial blood pressure curves, may serve as alternative cardiac noninvasive assisting device that enables the use of the apparatus in a wide range of acute and chronic heart failure cases.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

What is claimed is:

1. An ambient pressure control ventilation method for mechanical ventilation of a patient comprising the following steps:

providing a sealable chamber adapted to accommodate a whole body of a patient;

providing a pump fluidically connected to said chamber adapted to alternatively compress and decompress a ventilating gas within said chamber;

providing a relief valve, fluidically connected to said chamber;

providing a control unit adapted to control said pump and said relief valve so as to facilitate a periodic regime of alternating compression and decompression of said ventilating gas within said chamber, about a predetermined baseline;

placing a whole body of a patient in said sealable chamber; and providing a periodic regime of alternating compression and decompression of a ventilating gas within said chamber, about a predetermined baseline.

2. The method as claimed in claim 1, wherein said ventilating gas is a mixture of oxygen and air.

3. The method as claimed in claim 1, wherein said baseline ranges between 0.5 atm. and 1.5 atm.

4. The method as claimed in claim 3, wherein the periodic regime of alternating compression and decompression of said ventilating gas within said chamber alternates between said baseline plus 170 mm Hg to said baseline minus 170 mm Hg.

5. The method as claimed in claim 1, wherein the baseline is the ambient barometric pressure.

6. The method as claimed in claim 1, wherein the periodic regime of alternating compression and decompression of said ventilating gas within said chamber, alternates between the ambient barometric pressure to the ambient barometric pressure plus 175 mm Hg.

7. The method as claimed in claim 1, wherein the periodic regime of alternating compression and decompression of said ventilating gas within said chamber, alternates between the ambient barometric pressure minus 90 mm Hg to the ambient barometric pressure plus 90 mm Hg.

8. The method as claimed in claim 1, further comprising the step of compressing into said chamber an additional volume of oxygen upon an oxygen partial pressure drop below a predetermined value within said chamber.

9. The method as claimed in claim 8, wherein said predetermined value is 0.25 atm.

* * * * *